United States Patent [19]
Shimasaki et al.

[11] Patent Number: 5,625,076
[45] Date of Patent: Apr. 29, 1997

[54] CATALYST FOR PRODUCTION OF TERTIARY N-ALKENYL CARBOXYLIC ACID AMIDE, AND PROCESS FOR PRODUCTION OF TERTIARY N-ALKENYL CARBOXYLIC ACID AMIDE USING SAID CATALYST

[75] Inventors: Yuuji Shimasaki, Otsu; Hitoshi Yano; Kimio Ariyoshi, both of Suita, all of Japan

[73] Assignee: Nippon Shokubai Co., Ltd., Osaka, Japan

[21] Appl. No.: 529,324

[22] Filed: Sep. 18, 1995

[30] Foreign Application Priority Data

Sep. 19, 1994 [JP] Japan .................................. 6-222895

[51] Int. Cl.$^6$ .................... C07C 231/12; C07D 207/26
[52] U.S. Cl. .................... 548/552; 548/543; 564/215
[58] Field of Search .................... 548/543, 552; 564/215

[56] References Cited

U.S. PATENT DOCUMENTS

| | | | |
|---|---|---|---|
| 2,669,570 | 2/1954 | Schnizer | 260/326.5 |
| 2,775,599 | 12/1956 | Puetzer et al. | 260/326.5 |
| 3,821,245 | 6/1974 | Kanetake et al. | 260/326.5 FN |
| 4,567,300 | 1/1986 | Murao et al. | 564/215 |
| 5,410,070 | 4/1995 | Franz et al. | 548/552 |
| 5,527,963 | 6/1996 | Sato et al. | 564/214 |

FOREIGN PATENT DOCUMENTS

| | | |
|---|---|---|
| 0227461 | 7/1987 | European Pat. Off. . |
| 0228898 | 7/1987 | European Pat. Off. . |
| 0230776 | 8/1987 | European Pat. Off. . |
| 0489166 | 6/1992 | European Pat. Off. . |
| 0608690 | 8/1994 | European Pat. Off. . |
| 47-18862 | 9/1972 | Japan . |
| 47-40792 | 10/1972 | Japan . |
| 48-44251 | 6/1973 | Japan . |
| 6256306 | 9/1994 | Japan . |

Primary Examiner—Richard L. Raymond
Attorney, Agent, or Firm—Sherman and Shalloway

[57] ABSTRACT

The present invention provides a catalyst which is an oxide comprising silicon and at least one element selected from the group consisting of alkali metals and alkaline earth metals and which is used for gas-phase intramolecular dehydration of a tertiary N-(2-hydroxyalkyl) carboxylic acid amide to synthesize a tertiary N-alkenyl carboxylic acid amide. This catalyst enables continuous and efficient production of a tertiary N-alkenyl carboxylic acid amide from a tertiary N-(2-hydroxyalkyl) carboxylic acid amide without using any auxiliary raw material, and consequently allows for simple and safe production of a tertiary N-alkenyl carboxylic acid amide without generating any by-product (waste product) derived from the auxiliary raw material.

6 Claims, No Drawings

CATALYST FOR PRODUCTION OF TERTIARY N-ALKENYL CARBOXYLIC ACID AMIDE, AND PROCESS FOR PRODUCTION OF TERTIARY N-ALKENYL CARBOXYLIC ACID AMIDE USING SAID CATALYST

The present invention relates to a catalyst for production of a tertiary N-alkenyl carboxylic acid amide, as well as to a process for production of a tertiary N-alkenyl carboxylic acid amide using said catalyst.

N-Alkenyl-N'-alkyl-amide compounds and N-alkenyl-2-pyrrolidones are useful as raw material monomers for production of poly(N-vinyl-amine)s extensively used as raw materials for flocculants, paper-making chemicals, petroleum-drilling chemicals, textile chemicals, resin additives, etc.

The disclosed processes for production of a tertiary N-alkenyl carboxylic acid amide include the followings.

(a) Process for production of N-vinyl-N'-alkyl-amide compound

A process is well known which comprises reacting a N,N'-dialkylamide compound with acetylene in the presence of a basic catalyst at a high temperature at a high pressure to produce an N-vinyl-N'-alkyl-amide compound (this is a Reppe process). This process, however, generates a bisethylidene type by-product formed by the reaction of 2 moles of an N,N'-dialkylamide compound and 1 mole of acetylene, and resultantly has a low yield generally. Moreover, there is a danger of acetylene decomposition and explosion.

Alternatively, there are known a process by dehydrohalogenation of N-halogenated ethyl-N'-alkyl-amide compound, a process by acetic acid elimination from N-acetoxylated ethyl compound, and other processes. These processes, however, have various problems. That is, it is not easy to procure raw materials, and synthesis of such raw materials requires a high cost in some cases; further, large amounts of by-products are generated in N-vinylation and the recovery and disposal of such by-products need much labor and a large expense. Thus, these processes are not advantageous industrially.

If an N-vinyl-N'-alkyl-amide compound could be produced, at a high yield, by intramolecular dehydration of an N-(2-hydroxyethyl)-N'-alkyl-amide compound which can be easily produced by a reaction of an organic carboxylic acid of high industrial availability or an ester thereof with a 2-alkylamino-1-ethanol compound, or by a reaction of an N,N'-dialkylamide compound with oxirane or ethylene carbonate, the process could become a process for production of an N-vinyl-N'-alkyl-amide compound, which process requires a low cost, can save labor and is advantageous industrially.

b) Process for production of N-vinyl-2-pyrrolidone

Currently, N-vinyl-2-pyrrolidone is being produced industrially by a Reppe process of reacting 2-pyrrolidone with acetylene in the presence of a catalyst according to the following reaction formula (7).

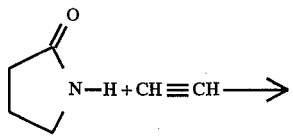

(7)

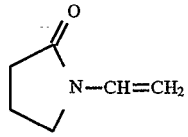

The process is carried out by a liquid phase reaction using an alkali catalyst under pressure. It, however, has various problems, for example, (1) acetylene may cause decomposition and explosion at high pressures, and (2) complex controls of reaction are necessary in catalyst preparation and pyrrolidone conversion order to prevent reduction in reaction yield.

Meanwhile, various processes using no acetylene have been attempted which use, as a raw material, an N-(2-hydroxyethyl)-2-pyrrolidone obtainable, at a high yield, by the reaction of γ-butyrolactone with monoethanolamine.

That is, there were proposed, for example, a process represented by the following reaction formula (8), disclosed in U.S. Pat. No. 2,775,599, that is, a process of subjecting, to dehydrochlorination, an N-(2-chloroethyl)-2-pyrrolidone obtained by the reaction of an N-(2-hydroxyethyl )-2-pyrrolidone with thionyl chloride; and a process represented by the following reaction formula (9), that is, a process of subjecting, to acetic acid elimination, an acetic acid ester intermediate obtained by the reaction of an N-(2-hydroxyethyl)-2-pyrrolidone with acetic anhydride. These processes via an intermediate, however, have various problems. That is, an auxiliary raw material is required in an amount equivalent to that of N-(2-hydroxyethyl )-2-pyrrolidone; the cost of intermediate production is large; and by-product are generated from the auxiliary raw material in large amounts; thus, these processes are not advantageous industrially.

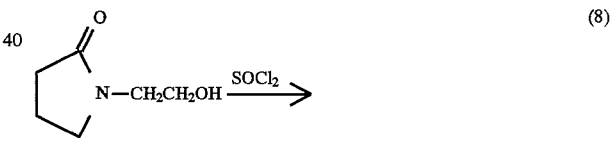

(8)

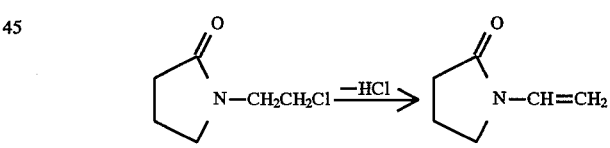

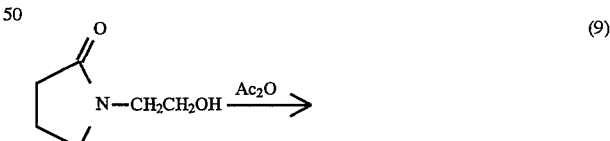

(9)

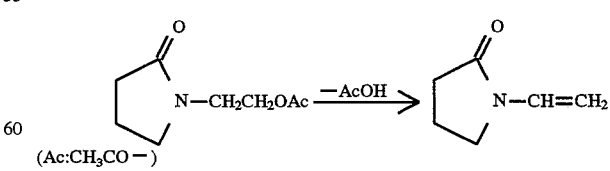

(Ac:CH₃CO—)

In order to solve these problems, there was proposed a process represented by the following reaction formula (10), that is, a process of subjecting N-(2-hydroxyethyl)-2-pyrrolidone to gas-phase intramolecular dehydration in the presence of a catalyst to produce N-2-vinyl-2-pyrrolidone.

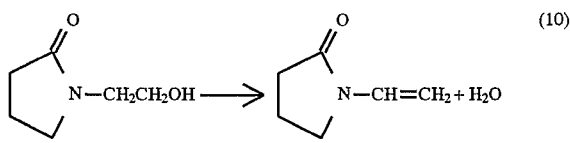

(10)

In this process, it is important that the catalyst used has a high catalytic activity and a high selectivity and further the catalytic activity is stable with the lapse of time. There are disclosed, as the catalyst, active alumina in U.S. Pat. No. 2,669,570; cerium oxide, zinc oxide, chromium oxide, etc. in Japanese Patent Application Kokai (Laid-Open) No. 18862/1972; zirconium oxide and thorium oxide in Japanese Patent Publication No. 40792/1972; lanthanum oxide, neodymium oxide, etc. in Japanese Patent Application Kokai (Laid-Open) No. 44251/1973; and acidic heterogeneous catalysts other than the oxides of metals of group IIb (zinc, cadmium and mercury), group IIIb (scandium and yttrium), group IVb (titanium, zirconium and hafnium) and group VIb (chromium, molybdenum and tungsten) in Japanese Patent Application Kokai (Laid-Open) No. 256306/1994.

The active alumina disclosed in U.S. Pat. No. 2,669,570, however, is not advantageous from the industrial standpoints such as process economy, separation and purification of product, and the like because with this catalyst, as indicated in Reference Example of Japanese Patent Publication No. 40792/1972, the reactivity (conversion) of N-(2-hydroxyethyl)-2-pyrrolidone is as low as 31.7 mole %, the yield (selectivity) of N-vinyl-2-pyrrolidone relative to N-(2-hydroxyethyl)-2-pyrrolidone reacted is as low as 62.8 mole %, and the proportion of by-product polymer is as high as 22.8 mole %. Of other catalysts, zirconium oxide has the highest performance. It is disclosed in Example 6 of Japanese Patent Publication No. 40792/1972 that with zirconium oxide, N-vinyl-2-pyrrolidone and 2-pyrrolidone are obtained at selectivities of 92.6 mole % and 5.6 mole %, respectively, at a conversion of N-(2-hydroxyethyl)-2-pyrrolidone of 88.6 mole %. This catalytic performance is relatively high, but a catalyst capable of exhibiting a higher selectivity and a stable activity with the lapse of time is required for efficient industrial production of N-vinyl-2-pyrrolidone. Incidentally, in the experiment conducted by the present inventors using zirconiunm oxide under the same reaction conditions as in the above invention (Japanese Patent Publication No. 40792/1972), the conversion of N-(2-hydroxyethyl) -2-pyrrolidone was as high as 84.7 mole % but the selectivity of N-vinyl-2-pyrrolidone was not necessarily satisfactory at 71.0 mole %, as shown in Comparative Example 2 of the present invention which appears later.

As mentioned previously, Japanese Patent Application Kokai (Laid-Open) No. 256306/1994 discloses a process using acidic heterogeneous catalysts other than the oxides of metal s of group IIb (zinc, cadmium and mercury), group IIIb (scandium and yttrium), group IVb (titanium, zirconium and hafnium) and group VIb (chromium, molybdenum and tungsten). In this disclosure, part of the catalyst elements mentioned in other prior art is excluded intentionally and all of the non-excluded elements appear to be effective; therefore, the catalysts usable in the disclosure are too broad and ambiguous. As well known, different catalysts containing the same element, differ greatly in their performances, depending upon their compositions, calcination temperatures employed during preparation, etc. In the above literature, however, no specific description is given on the catalyst used. In the Examples of the litrature, only two specific catalysts, i.e. $H_3PO_4$ and $La(H_2PO_4)_3$ are mentioned; with these catalysts, the selectivity of N-vinyl-2-pyrrolidone in the dehydration of N-(2-hydroxyethyl)-2-pyrrolidone is relatively good at 80–90% but is not satisfactory industrially; moreover, the activity stability of these catalysts with the lapse of time is not sufficient, either.

Thus, in industrial production of N-vinyl-2-pyrrolidone by gas-phase intramolecular dehydration of N-(2-hydroxyethyl)-2-pyrrolidone in the presence of a catalyst, there is needed a high-performance catalyst capable of producing N-vinyl-2-pyrrolidone at a high selectivity. However, no catalyst having satisfactory performance has not yet been developed.

An object of the present invention is to provide a catalyst used for subjecting, to gas-phase intramolecular dehydration, a tertiary N-(2-hydroxyalkyl) carboxylic acid amide without using any auxiliary raw material to produce a tertiary N-alkenyl carboxylic acid amide at a very high selectivity and at a high yield.

Other object of the present invention is to provide a simple and efficient process for producing a tertiary N-alkenyl carboxylic acid amide at a very high selectivity and at a high yield by subjecting, to gas-phase intramolecular dehydration, a tertiary N-(2hydroxyalkyl) carboxylic acid amide without using any auxiliary raw material (consequently, without generating any waste product derived from the auxiliary raw material).

In order to find out a process which is free from the above-mentioned problems of the prior art and which can produce a tertiary N-alkenyl carboxylic acid amide simply and efficiently, the present inventors made a study on a catalyst capable of giving rise to the gas-phase intramolecular dehydration of a terriary N-(2-hydroxyalkyl) carboxylic acid amide. As a result, the present inventors found out that an oxide containing silicon and at least one elements selected from alkali metals and alkaline earth metals is an efficient catalyst for producing a tertiary N-alkenyl carboxylic acid amide from a tertiary N-(2-hydroxyalkyl) carboxylic acid amide at a high selectivity and at a high yield stably over a long period of time.

According to the present invention, there is provided a catalyst which is an oxide comprising silicon and at least one element selected from the group consisting of alkali metal s and alkaline earth metals and which is used for gas-phase intramolecular dehydration of a tertiary N-(2-hydroxyalkyl) carboxylic acid amide to synthesize a tertiary N-alkenyl carboxylic acid amide.

According to the present invention, there is also provided a process for producing a tertiary N-alkenyl carboxylic acid amide by gas-phase intramolecular dehydration of a tertiary N-(2-hydroxyalkyl) carboxylic acid amide, wherein the above-mentioned catalyst is used.

The present invention is hereinafter described in detail.

The catalyst of the present invention acts very effectively in subjecting, to gas-phase intramolecular dehydration, N-(2-hydroxyethyl)-2-pyrrolidone or a tertiary N-(2-hydroxyalkyl) carboxylic acid amide represented by the following general formula (2) or (4) to produce a corresponding tertiary N-alkenyl carboxylic acid amide.

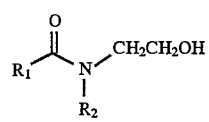

(2)

(wherein $R_1$ and $R_2$ are independently a hydrocarbon group of 1–6 carbon atoms).

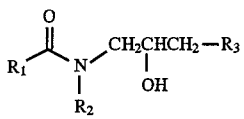

(wherein $R_1$, $R_2$ and $R_3$ are independent groups with $R_1$ and $R_2$ being each a hydrocarbon group of 1–6 carbon atoms and $R_3$ being a hydrogen atom or a hydrocarbon group of 1–6 carbon atoms).

The raw material used in the present invention is any tertiary N-(2-hydroxyalkyl) carboxylic acid amide such as mentioned above. Preferable specific examples thereof are N-(2-hydroxyethyl) or N-(2-hydroxypropyl) derivatives of N-methyl-acetamide, N-ethyl-acetamide, N-propyl-acetamide and N-butyl-acetamide; N-(2-hydroxyethyl) or N-(2-hydroxypropyl) derivatives of N-methyl-propylamide, N-ethyl-propylamide, N-propyl-propylamide and N-butyl-propylamide; and N-(2-hydroxyethyl)-2-pyrrolidone. The raw material not restricted to these. The N-(2-hydroxyethyl) derivatives can give corresponding terriary N-vinyl carboxylic acid amide compounds, and the N-(2-hydroxypropyl) derivatives can give corresponding tertiary N-(1-propenyl) carboxylic acid amides and tertiary N-(2-propenyl) carboxylic acid amides.

With the present catalyst, carbon (coke) deposition, i.e. coking on catalyst (this problem often takes place in the reactions of this type) is very low and the catalytic activity hardly decreases during the long-term continuous use of catalyst. Once the coking has proceeded, the reaction is stopped and an oxygen-containing gas is passed through the catalyst to burn and remove the coke deposited on the catalyst, whereby the reaction can be resumed.

The biggest effect of the present catalyst on the reaction of the present process lies in a very high selectivity of tertiary N-alkenyl carboxylic acid amide, which is unseen with the catalysts of prior art. This is made possible mainly because the present catalyst suppresses the decomposition and decarbonylation of tertiary N-(2-hydroxyalkyl) carboxylic acid amide used as raw material. In the case of production of, for example, N-vinyl-2-pyrrolidone, the decomposition of N-(2-hydroxyethyl)-2-pyrrolidone (raw material) into 2-pyrrolidone and acetaldehyde is greatly suppressed as compared with the case using a conventional catalyst.

The catalyst of the present invention is an oxide containing silicon and at least one element selected from alkali metals and alkaline earth metals, and is preferably an oxide represented by the following general formula (1)

wherein M is at least one element selected from the group consisting of alkali metals and alkaline earth metals; Si is silicon; X is at least one element selected from the group consisting of boron, aluminum and phosphorus; O is oxygen; a, b, c and d are each the number of atoms of the corresponding element with provisos that when a=1, b=1–500 and c=0–1 and that d is a number determined by the values of a, b and c and the condition in which the individual constituent elements are bonded to each other. The ratio of at least one element selected from alkali metals and alkaline earth metals, to silicon is 1:1 to 1:500, preferably 1:5 to 1:200. The appropriate ratio of at least one element selected from alkali metals and alkaline earth metals, to X (at least one element selected from boron, aluminum and phosphorus) added as necessary is 1:0 to 1:1.

There is no particular restriction as to the method for preparation of the present catalyst, and the catalyst can be prepared by any conventional method. The raw material for the at least one element selected from alkali metals and alkaline earth metals (which is an essential element of the present catalyst) can be an oxide, a hydroxide, a halide, a salt (e.g. a carbonic acid salt, a nitric acid salt, a carboxylic acid salt, a phosphoric acid salt or a sulfuric acid salt), a metal itself, etc. The raw material for silicon (which is another essential element) can be silicon oxide, silicic acid, a silicic acid salt (e.g. an alkali metal silicate or an alkaline earth metal silicate), a silicon-containing molecular sieve (e.g. aluminosilicate or silico-aluminophosphate), an organic silicic acid ester, etc. The raw material for X added as necessary can be an oxide, a hydroxide, a halide, a salt (e.g. a carbonic acid salt, a nitric acid salt, a carboxylic acid salt, phosphoric acid salt or a sulfuric acid salt), a metal itself, etc.

Specific examples of the preferable method for preparation of the present catalyst are described below.

(1) A method which comprises dissolving or suspending, in water, a raw material for silicon and a raw material for at least one element selected form alkali metals and alkaline earth metals, concentrating the aqueous solution or suspension with heating and stirring, followed by drying and calcining, to obtain a catalyst.

(2) A method which comprises dissolving, in water, a raw material for at least one element selected form alkali metals and alkaline earth metals, dipping molded silicon oxide in the aqueous solution, followed by evaporation to dryness, drying and calcining, to obtain a catalyst.

(3) A method which comprises dissolving, in water, a raw material for at least one element selected form alkali metals and alkaline earth metals, adding the aqueous solution to a silicic acid salt or an organic silicic acid ester, followed by mixing, drying and calcining, to obtain a catalyst.

(4) A method which comprises loading at least one element selected form alkali metals and alkaline earth metals, on a silicon-containing molecular sieve by ion exchange, followed by drying and calcining, to obtain a catalyst.

The component X may be added in any step of catalyst preparation before drying. For example, the component X may be present al ready in the raw material for at least one element selected form alkali metals and alkaline earth metals, and/or in the raw material for silicon. Or, the raw material for the component X may be added independently during the catalyst preparation.

The catalyst of the present invention may be supported on a known carrier such as alumina, silicon carbide or the like, or may be used in admixture with said carrier.

The calcination temperature of catalyst differs depending upon the composition of catalyst prepared or the kinds of catalyst raw materials used, but can be in a wide range of 300°–1,000° C. and preferably in the range of 400°–800° C.

The present process for production of tertiary N-alkenyl carboxylic acid amide comprises subjecting a tertiary N-(2-hydroxyalkyl) carboxylic acid amide to gas-phase intramolecular dehydration using the above-mentioned catalyst.

The process according to the present invention can be carried out in any reactor of fixed bed type, fluidized bed type or moving bed type. The reaction is conducted in such pressure and temperature that the raw material, i.e. the tertiary N-(2-hydroxyalkyl) carboxylic acid amide can maintain a gaseous state. The appropriate reaction temperature is 300°–500° C., preferably 350°–450° C. When the reaction temperature is lower than 300° C., the conversion of the raw material [tertiary N-(2-hydroxyalkyl) carboxylic acid amide] is significanfly low, which incurs reduced productivity. When the reaction temperature is higher than 500° C., the degree of side reactions increases [this invites significant reduction in selectivity of intended product (tertiary N-alkenyl carboxylic acid amide)] and the rate of coke formation increases (this invites significant reduction in catalyst activity).

There is no particular restriction as to the reaction pressure as long as the partial pressure of the raw material [tertiary N-(2-hydroxyalkyl) carboxylic acid amide] is controlled in the range of 5–600 mmHg, preferably 10–300 mmHg. When the partial pressure of the raw material is smaller than 5 mmHg, the reaction itself proceeds with no problem but the collection of product is difficult and/or a large apparatus for collection is required, inviting reduced productivity. When the partial pressure is larger than 600 mmHg, the degree of side reactions increases and the selectivity of intended product (tertiary N-alkenyl carboxylic acid amide) decreases. The preferable specific method for conducting the reaction of the present process while controlling the partial pressure of the raw material, include the followings.

(1) A method which comprises diluting the raw material with a gas (e.g. nitrogen, helium, argon or hydrocarbon) inert to the present reaction to control the partial pressure of the raw material at a desired level and passing the resulting gas through the present catalyst to give rise to a reaction. (In this case, the reaction pressure can be selected as desired.)

(2) A method which comprises passing the raw material alone through the catalyst with the reaction system kept at a reduced pressure to give rise to a reaction under a controlled partial pressure of raw material.

The gas hourly space velocity (GHSV), which is the amount of the raw material [terriary N-(2-hydroxyalkyl) carboxylic acid amide] fed per unit catalyst volume per unit time, differs slightly depending upon the kind of raw material, the conditions and method of reaction, etc., but is 1–1,000 $h^{-1}$, preferably 10–500 $h^{-1}$ in terms of the gas volume of tertiary N-(2-hydroxyalkyl) carboxylic acid amide at standard state (25° C. and 1 atm.). When the space velocity is smaller than 1 $h^{-1}$, the contact time is too long, which invites successive reactions and reduction in selectivity of intended product. When the space velocity is larger than 1,000 $h^{-1}$ the contact time is too short, which invites reduction in-conversion.

The present invention is hereinafter described specifically by way of Examples. However, the present invention is in no way restricted to the Examples.

Incidentally, the conversion, selectivity and per-pass yield used in the Examples have the following definitions.

Conversion (mole %)=100×[moles of consumed tertiary N-(2-hydroxyalkyl) carboxylic acid amide] /[moles of fed tertiary N-(2-hydroxyalkyl) carboxylic acid amide]

Selectivity (mole %)=100×[moles of produced tertiary N-alkenyl carboxylic acid amide] /[moles of consumed terriary N-(2-hydroxyalkyl) carboxylic acid amide]

Per-pass yield (%)=100×[moles of produced tertiary N-alkenyl carboxylic acid amide] /[moles of fed tertiary N-(2-hydroxyalkyl) carboxylic acid amide]

Examples 1–35 given below are each an example of production of a tertiary N-vinyl carboxylic acid amide by intramolecular dehydration of a tertiary N-(2-hydroxyethyl) carboxylic acid amide.

EXAMPLE 1

(Catalyst Preparation)
0.7 g of lithium hydroxide monohydrate was dissolved in 100 g of water. Therein was dipped 30 g of spherical silica gel (5–10 mesh) for 2 hours. The resulting material was subjected to evaporation to dryness on a water bath, followed by drying in air at 120° C. for 20 hours and subsequent calcining in air at 600° C. for 2 hours, to obtain a catalyst having a composition of $Li_1Si_{30}$ in terms of atomic ratio when oxygen was excluded.

(Reaction)
5 ml of the catalyst was filled in a stainless steel-made reaction tube having an inside diameter of 10 mm, and the reaction tube was dipped in a molten salt bath of 380° C. Into the reaction tube was fed a raw material gas consisting of N-(2-hydroxyethyl)-N'-methyl-acetamide and nitrogen used as a diluent (the partial pressure of said acetamide in the raw material gas was 76 mmHg), at a space velocity (of said acetamide) of 200 $h^{-1}$, to give rise to a reaction at normal pressure. One hour after the start of the reaction, the gas at the reaction tube outlet was analyzed by gas chromatography. As a result, the conversion of N-(2-hydroxyethyl)-N'-methyl-acetamide and the selectivity and per-pass yield of N-vinyl-N'-methyl-acetamide were 73.6 mole %, 89.2 mole % and 65.7 mole %, respectively.

EXAMPLE 2

(Catalyst Preparation)
0.43 g of sodium nitrate was dissolved in 100 g of water. Therein was dipped 30 g of spherical silica gel (5–10 mesh) for 2 hours. The resulting material was subjected to evaporation to dryness on a water bath, followed by drying in air at 120° C. for 20 hours and subsequent calcining in air at 600° C. for 2 hours, to obtain a catalyst having a composition of $Na_1Si_{100}$ in terms of atomic ratio when oxygen was excluded.

(Reaction)
A reaction was conducted with the catalyst in the same manner as in Example 1 except that the reaction temperature was 400° C., after which analysis was made also in the same manner as in Example 1. One hour after the start of the reaction, the conversion of N-(2-hydroxyethyl)-N'-methyl-acetamide and the selectivity and per-pass yield of N-vinyl-N'-methyl-acetamide were 75.2 mole %, 87.1 mole % and 65.5 mole %, respectively.

EXAMPLE 3

(Catalyst Preparation)
5.06 g of potassium nitrate was dissolved in 250 g of water, and the solution was kept at 90° C. with stirring. Thereto was added 30 g of silicon oxide. The mixture was concentrated with heating and the concentrate was dried in air at 120° C. for 20 hours. The resulting solid was crushed into particles of 9–16 mesh and calcined in air at 500° C. for 2 hours to obtain a catalyst having a composition of $K_1Si_{10}$ in terms of atomic ratio when oxygen was excluded.

(Reaction)
A reaction was conducted with the catalyst in the same manner as in Example 1 except that the reaction temperature was 390° C., after which analysis was made also in the same manner as in Example 1. One hour after the start of the reaction, the conversion of N-(2-hydroxyethyl)-N'-methyl-acetamide and the selectivity and per-pass yield of N-vinyl-N'-methyl-acetamide were 77.3 mole %, 85.6 mole % and 66.1 mole %, respectively.

EXAMPLE 4

(Catalyst Preparation)
7.38 g of rubidium nitrate was dissolved in 250 g of water, and the solution was kept at 90° C. with stirring. Thereto was added 30 g of silicon oxide. The mixture was concentrated with heating and the concentrate was dried in air at 120° C.

for 20 hours. The resulting solid was crushed into particles of 9–16 mesh and calcined in air at 500° C. for 2 hours to obtain a catalyst having a composition of $Rb_1Si_{10}$ in terms of atomic ratio when oxygen was excluded.
(Reaction)

A reaction was conducted with the catalyst in the same manner as in Example 1, after which analysis was made also in the same manner as in Example 1. One hour after the start of the reaction, the conversion of N-(2-hydroxyethyl)-N'-methyl-acetamide and the selectivity and per-pass yield of N-vinyl-N'-methyl-acetamide were 74.9 mole %, 88.8 mole % and 66.5 mole %, respectively.

EXAMPLE 5

(Catalyst Preparation)

7.76 g of cesium carbonate was dissolved in 250 g of water, and the solution was kept at 90° C. with stirring. Thereto was added 30 g of silicon oxide. The mixture was concentrated with heating and the concentrate was dried in air at 120° C. for 20 hours. The resulting solid was crushed into particles of 9–16 mesh and calcined in air at 500° C. for 2 hours to obtain a catalyst having a composition of $Cs_1Si_{10}$ in terms of atomic ratio when oxygen was excluded.
(Reaction)

A reaction was conducted with the catalyst in the same manner as in Example 1, after which analysis was made also in the same manner as in Example 1. One hour after the start of the reaction, the conversion of N-(2-hydroxyethyl)-N'-methyl-acetamide and the selectivity and per-pass yield of N-vinyl-N'-methyl-acetamide were 76.2 mole %, 89.1 mole % and 67.9 mole %, respectively.

EXAMPLE 6

(Catalyst Preparation)

8.15 g of cesium carbon ate, 0.66 g of diammonium phosphate and 30 g of silicon oxide were added to 150 g of water. The mixture was concentrated to dryness with stirring and heating on a water bath. The resulting material was dried in air at 120° C. for 20 hours and crushed into particles of 9–16 mesh, followed by calcining in air at 450° C. for 2 hours, to obtain a catalyst having a composition of $Cs_1Si_{10}P_{0.1}$ in terms of atomic ratio when oxygen was excluded.
(Reaction)

A reaction was conducted with the catalyst in the same manner as in Example 1 except that the partial pressure and space velocity of N-(2-hydroxyethyl)-N'-methyl-acetamide were changed to 38 mmHg and 100 h$^{-1}$, respectively, after which analysis was made also in the same manner as in Example 1. One hour after the start of the reaction, the conversion of N-(2-hydroxyethyl)-N'-methyl-acetamide and the selectivity and per-pass yield of N-vinyl-N'-methyl-acetamide were 73.9 mole %, 92.6 mole % and 68.4 mole %, respectively.

EXAMPLE 7

A reaction was conducted with the catalyst of Example 1 except that the raw material for reaction was changed to N-(2-hydroxyethyl)-N'-methyl-propylamide, after which analysis was made also in the same manner as in Example 1. One hour after the start of the reaction, the conversion of N-(2-hydroxyethyl)-N'-methyl-propylamide and the selectivity and per-pass yield of N-vinyl-N'-methyl-propylamide were 87.1 mole %, 91.3 mole % and 79.5 mole %, respectively.

EXAMPLE 8

(Catalyst Preparation)

0.29 g of magnesium hydroxide, 6.64 g of rubidium nitrate and 30 g of silicon oxide were added to 150 g of water. The mixture was concentrated to dryness with stirring and heating on a water bath. The resulting material was dried in air at 120° C. for 20 hours and crushed into particles of 9–16 mesh, followed by calcining in air at 500° C. for 2 hours, to obtain a catalyst having a composition of $Rb_{0.9}Mg_{0.1}Si_{10}$ in terms of atomic ratio when oxygen was excluded.
(Reaction)

A reaction was conducted with the catalyst in the same manner as in Example 6, after which analysis was made also in the same manner as in Example 7. One hour after the start of the reaction, the conversion of N-(2-hydroxyethyl)-N'-methyl-propylamide and the selectivity and per-pass yield of N-vinyl-N'-methyl-propylamide were 85.4 mole %, 93.1 mole % and 79.1 mole %, respectively.

EXAMPLE 9

(Catalyst Preparation)

3.16 g of barium hydroxide octahydrate, 7.80 g of cesium nitrate and 30 g of silicon oxide were added to 150 g of water. The mixture was concentrated to dryness with stirring and heating on a water bath. The resulting material was dried in air at 120° C. for 20 hours and crushed into particles of 9–16 mesh, followed by calcining in air at 500° C. for 2 hours, to obtain a catalyst having a composition of $Cs_{0.8}Ba_{0.2}Si_{10}$ in terms of atomic ratio when oxygen was excluded.
(Reaction)

A reaction was conducted with the catalyst in the same manner as in Example 6, after which analysis was made also in the same manner as in Example 7. One hour after the start of the reaction, the conversion of N-(2-hydroxyethyl)-N'-methyl-propylamide and the selectivity and per-pass yield of N-vinyl-N'-methyl-propylamide were 87.1 mole %, 92.4 mole % and 80.5 mole %, respectively.

EXAMPLE 10

(Catalyst Preparation)

1.40 g of potassium hydroxide and 0.15 g of boric acid were dissolved in 100 g of water. In the solution was dipped 30 g of a spherical silica gel (5–10 mesh) for 3 hours. The resulting material was concentrated to dryness on a water bath, followed by drying in air at 120° C. for 20 hours and subsequent calcining in air at 600° C. for 2 hours, to obtain a catalyst having a composition of $K_1Si_{20}$ $_{1\ B0.1}$ in terms of atomic ratio when oxygen was excluded.
(Reaction)

A reaction was conducted with the catalyst in the same manner as in Example 6, after which analysis was made also in the same manner as in Example 7. One hour after the start of the reaction, the conversion of N-(2-hydroxyethyl)-N'-methyl-propylamide and the selectivity and per-pass yield of N-vinyl-N'-methyl-propylamide were 88.8 mole %, 91.4 mole % and 81.2 mole %, respectively.

EXAMPLE 11

(Reaction)

5 ml of the catalyst of Example 1 was filled in a stainless steel-made reaction tube having an inside diameter of 10 mm. The reaction tube was dipped in a molten salt bath of 370° C. By providing a vacuum pump at the back end of the reaction tube, the outlet pressure of the reaction tube was control led at 38 mmHg. Into this reaction tube was fed N-(2-hydroxyethyl)-N'-methyl-propylamide at a space velocity of 100 h$^{-1}$ to give rise to a reaction. After 50 hours of the reaction, the feeding of the raw material was stopped, and the pressure inside the reaction tube was returned to normal with nitrogen. Then, air was passed through the reaction tube at a rate of 100 cc/min for 24 hours to burn and remove the carbonaceous substance deposited on the catalyst, whereby the catalyst was regenerated. Thereafter, a reaction was conducted for 50 hours under the same conditions as mentioned above. The outlet gases of the reaction tube after 1 hour and 50 hours from the start of the raw material feeding and after 1 hour and 50 hours after the catalyst regeneration were analyzed by gas chromatography. The conversions of N-(2-hydroxyethyl)-N'-methyl-propylamide and the selectivities and per-pass yields of N-vinyl-N'-methyl-propylamide were as shown in Table 1.

TABLE 1

| Time (hour) | Conversion (mole %) | Selectivity (mole %) | Per-pass yield (mole %) |
|---|---|---|---|
| 1 | 86.4 | 94.2 | 81.4 |
| 50 | 80.0 | 95.6 | 76.5 |
| After regeneration | | | |
| 1 | 86.6 | 94.3 | 81.7 |
| 50 | 80.1 | 95.8 | 76.7 |

EXAMPLE 12

(Catalyst Preparation)

3.45 g of lithium nitrate was dissolved in 50 g of water, and the solution was kept at 90° C. with stirring. Thereto was added 30 g of silicon oxide. The mixture was concentrated with heating and the concentrate was dried in air at 120° C. for 20 hours. The resulting solid was crushed into particles of 9–16 mesh and calcined in air at 500° C. for 2 hours to obtain a catalyst having a composition of $Li_1Si_{10}$ in terms of atomic ratio when oxygen was excluded.

(Reaction)

5 ml of the catalyst was filled in a stainless steel-made reaction tube having an inside diameter of 10 mm, and the reaction tube was dipped in a molten salt bath of 400° C. Into the reaction tube was fed a raw material gas consisting of N-(2-hydroxyethyl)-2-pyrrolidone and nitrogen used as a diluent (the partial pressure of said pyrrolidone in the raw material gas was 76 mmHg), at a space velocity (of said pyrrolidone) of 200 h$^{-1}$, to give rise to a reaction at normal pressure. One hour after the start of the reaction, the gas at the reaction tube outlet was analyzed by gas chromatography. As a result, the conversi on of N-(2-hydroxyethyl)-2-pyrrolidone and the selectivity and per-pass yield of N-vinyl-2-pyrrolidone were 59.2 mole %, 99.2 mole % and 58.7 mole %, respectively.

EXAMPLE 13–16

(Catalyst Preparation)

Catalysts having compositions (each expressed in terms of atomic ratio when oxygen was excluded) shown in Table 2 were obtained in the same manner as in Example 12 except that 3.45 g of lithium nitrate used in Example 12 was changed to 4.25 g of sodium nitrate (Example 13), 5.06 g of potassium nitrate (Example 14), 7.38 g of rubidium nitrate (Example 15) and 9.75 g of cesium nitrate (Example 16).

(Reaction)

Reactions were conducted with the catalysts prepared above, in the same manner as in Example 12 except that the reaction temperature used in Example 12 was changed as shown in Table 2, after which analyses were made in the same manner as in Example 12. One hour after the start of the reaction, the conversions of N-(2-hydroxyethyl)-2-pyrrolidone and the selectivities and per-pass yields of N-vinyl-2-pyrrolidone were as shown in Table 2.

TABLE 2

| Example No. | Catalyst | Reaction temp. (°C.) | Conversion (mole %) | Selectivity (mole %) | Per-pass yield (mole %) |
|---|---|---|---|---|---|
| 13 | $Na_1Si_{10}$ | 370 | 57.0 | 98.7 | 56.3 |
| 14 | $K_1Si_{10}$ | 370 | 85.9 | 95.1 | 81.7 |
| 15 | $Rb_1Si_{10}$ | 370 | 89.8 | 94.2 | 84.6 |
| 16 | $Cs_1Si_{10}$ | 350 | 80.9 | 96.2 | 77.8 |

COMPARATIVE EXAMPLE 1

A reaction was conducted in the same manner as in Example 12 except that the catalyst was changed to active alumina (calcining was conducted at 500° C. for 2 hours), after which analysis was made also in the same manner as in Example 12. One hour after the start of the reaction, the conversion of N-(2-hydroxyethyl)-2-pyrrolidone and the selectivity and per-pass yield of N-vinyl-2-pyrrolidone were 93.8 mole %, 33.6 mole % and 31.5 mole %, respectively.

COMPARATIVE EXAMPLE 2

A reaction was conducted in the same manner as in Example 12 except that the catalyst was changed to zirconium oxide (calcining was conducted at 900° C. for 2 hours) and the reaction temperature was changed to 370° C., after which analysis was made also in the same manner as in Example 12. One hour after the start of the reaction, the conversion of N-(2-hydroxyethyl)-2-pyrrolidone and the selectivity and per-pass yield of N-vinyl-2-pyrrolidone were 84.7 mole %, 71.0 mole % and 60.3 mole %, respectively.

COMPARATIVE EXAMPLE 3

A reaction was conducted in the same manner as in Example 12 except that the catalyst was changed to silicon oxide (calcining was conducted at 500° C. for 2 hours) and the reaction temperature was changed to 370° C., after which analysis was made also in the same manner as in Example 12. One hour after the start of the reaction, the conversion of N-(2-hydroxyethyl)-2-pyrrolidone and the selectivity and per-pass yield of N-vinyl-2-pyrrolidone were 16.3 mole %, 94.2 mole % and 15.4 mole %, respectively.

EXAMPLE 17

(Catalyst Preparation)

0.81 g of cesium carbonate was dissolved in 40 g of water. Therein was dipped 30 g of spherical silica gel (5–10 mesh) for 2 hours. The resulting material was subjected to evaporation to dryness on a water bath, followed by drying in air at 120° C. for 20 hours and subsequent calcining in air at 800° C. for 2 hours, to obtain a catalyst having a composition of $Cs_1Si_{100}$ in terms of atomic ratio when oxygen was excluded.

(Reaction)

A reaction was conducted with the catalyst in the same manner as in Example 12 except that the reaction temperature was changed to 360° C., after which analysis was made also in the same manner as in Example 12. One hour after the start of the reaction, the conversion of N-(2-hydroxyethyl)-2-pyrrolidone and the selectivity and per-pass yield of N-vinyl-2-pyrrolidone were 93.8 mole %, 93.1 mole % and 87.3 mole %, respectively.

EXAMPLE 18

(Catalyst Preparation)

A catalyst having a composition of $Cs_1Si_{200}$ in terms of atomic ratio when oxygen was excluded, was prepared in the same manner as in Example 17 except that the amount of cesium carbonate was changed from 0.81 g to 0.41 g.
(Reaction)

A reaction was conducted with the catalyst in the same manner as in Example 12 except that the reaction temperature was changed to 370° C., after which analysis was made also in the same manner as in Example 12. One hour after the start of the reaction, the conversion of N-(2-hydroxyethyl)-2-pyrrolidone and the selectivity and per-pass yield of N-vinyl-2-pyrrolidone were 90.7 mole %, 91.1 mole % and 82.6 mole %, respectively.

EXAMPLE 19

(Catalyst Preparation)

A catalyst having a composition of $Na_1Si_{30}$ in terms of atomic ratio when oxygen was excluded, was prepared in the same manner as in Example 17 except that cesium carbonate (0.81 g) was changed to sodium carbonate (0.88 g) and that the calcining temperature was changed to 700° C .
(Reaction)

A reaction was conducted with the catalyst in the same manner as in Example 12 except that the reaction temperature was changed to 370° C., after which analysis was made also in the same manner as in Example 12. One hour after the start of the reaction, the conversion of N-(2-hydroxyethyl)-2-pyrrolidone and the selectivity and per-pass yield of N-vinyl-2-pyrrolidone were 92.7 mole %, 92.1 mole % and 85.4 mole %, respectively.

EXAMPLE 20

(Catalyst Preparation)

A catalyst having a composition of $K_1Si_{30}$ in terms of atomic ratio when oxygen was excluded, was prepared in the same manner as in Example 17 except that cesium carbonate (0.81 g) was changed to potassium carbonate (1.15 g) and that the calcination temperature was changed to 700° C.
(Reaction)

A reaction was conducted with the catalyst in the same manner as in Example 12 except that the reaction temperature was changed to 370° C., after which analysis was made also in the same manner as in Example 12. One hour after the start of the reaction, the conversion of N-(2-hydroxyethyl)-2-pyrrolidone and the selectivity and per-pass yield of N-vinyl-2-pyrrolidone were 91.1 mole %, 91.8 mole % and 83.6 mole %, respectively.

EXAMPLE 21

(Catalyst Preparation)

A catalyst having a composition of $Rb_1Si_{30}$ in terms of atomic ratio when oxygen was excluded, was prepared in the same manner as in Example 17 except that cesium carbonate (0.81 g) was changed to rubidium carbonate (1.71 g) and that the calcination temperature was changed to 700° C.
(Reaction)

A reaction was conducted with the catalyst in the same manner as in Example 12 except that the reaction temperature was changed to 360° C., after which analysis was made also in the same manner as in Example 12. One hour after the start of the reaction, the conversion of N-(2-hydroxyethyl)-2-pyrrolidone and the selectivity and per-pass yield of N-vinyl-2-pyrrolidone were 93.5 mole %, 91.0 mole % and 85.1 mole %, respectively.

CATALYST 22

(Catalyst Preparation)

A catalyst having a composition of $Cs_1Si_{10}$ in terms of atomic ratio when oxygen was excluded, was prepared in the same manner as in Example 12 except that lithium nitrate (3.45 g) was changed to cesium hydroxide (7.5 g).
(Reaction)

A reaction was conducted with the catalyst in the same manner as in Example 12 except that the reaction temperature was changed to 360° C., after which analysis was made also in the same manner as in Example 12. One hour after the start of the reaction, the conversion of N-(2-hydroxyethyl)-2-pyrrolidone and the selectivity and per-pass yield of N-vinyl-2-pyrrolidone were 94.6 mole %, 94.6 mole % and 89.5 mole %, respectively.

EXAMPLE 23

(Catalyst Preparation)

2.9 g of magnesium hydroxide and 30 g of silicon oxide were added to 150 g of water. The mixture was concentrated to dryness with stirring and heating on a water bath. The resulting material was dried in air at 120° C. for 20 hours and crushed into particles of 9–16 mesh, followed by calcining in air at 500° C. for 2 hours, to obtain a catalyst having a composition of $Mg_1Si_{10}$ in terms of atomic ratio when oxygen was excluded.
(Reaction)

A reaction was conducted with the catalyst in the same manner as in Example 12, after which analysis was made also in the same manner as in Example 12. One hour after the start of the reaction, the conversion of N-(2-hydroxyethyl)-2-pyrrolidone and the selectivity and per-pass yield of N-vinyl-2-pyrrolidone were 54.6 mole %, 88.6 mole % and 48.4 mole %, respectively.

EXAMPLE 24–26

(Catalyst Preparation)

Catalysts having compositions (each expressed in terms of atomic ratio when oxygen was excluded) shown in Table 3 were obtained in the same manner as in Example 23 except that 2.9 g of magnesium hydroxide used in Example 23 was changed to 3.7 g of calcium hydroxide (Example 24), 13.3 g of strontium hydroxide octahydrate (Example 25) and 15.8 g of barium hydroxide octahydrate (Example 26).
(Reaction)

Reactions were conducted with the catalysts prepared above, in the same manner as in Example 12, after which analyses were made in the same manner as in Example 12. One hour after the start of the reaction, the conversions of N-(2-hydroxyethyl)-2-pyrrolidone and the selectivities and per-pass yields of N-vinyl-2-pyrrolidone were as shown in Table 3.

TABLE 3

| Example No. | Catalyst | Reaction temp. (°C.) | Conversion (mole %) | Selectivity (mole %) | Per-pass yield (mole %) |
| --- | --- | --- | --- | --- | --- |
| 24 | $Ca_1Si_{10}$ | 400 | 51.1 | 85.2 | 43.5 |
| 25 | $Sr_1Si_{10}$ | 400 | 58.9 | 89.2 | 52.5 |
| 26 | $Ba_1Si_{10}$ | 400 | 50.8 | 99.8 | 50.7 |

EXAMPLE 27

(Catalyst Preparation)

3.9 g of cesium nitrate and 0.34 g of lithium nitrate were dissolved in 100 g of water. Thereto was added 30 g of silicon oxide. The mixture was concentrated to dryness with stirring and heating on a water bath. The resulting material was dried in air at 120° C. for 20 hours and crushed into particles of 9–16 mesh, followed by calcining in air at 500° C. for 2 hours, to obtain a catalyst having a composition of $Cs_{0.8}Li_{0.2}Si_{20}$ in terms of atomic ratio when oxygen was excluded.

(Reaction)

A reaction was conducted with the catalyst in the same manner as in Example 12 except that the reaction temperature was changed to 350° C., after which analysis was made also in the same manner as in Example 12. One hour after the start of the reaction, the conversion of N-(2-hydroxyethyl)-2-pyrrolidone and the selectivity and per-pass yield of N-vinyl-2-pyrrolidone were 82.8 mole %, 94.3 mole % and 78.1 mole %, respectively.

EXAMPLE 28

(Catalyst Preparation)

5.9 g of rubidium nitrate and 3.2 g of barium hydroxide octahydrate were dissolved in 100 g of water. Thereto was added 30 g of silicon oxide. The mixture was concentrated to dryness with stirring and heating on a water bath. The resulting material was dried in air at 120° C. for 20 hours and crushed into particles of 9–16 mesh, followed by calcining in air at 500° C. for 2 hours, to obtain a catalyst having a composition of $Rb_{0.8}Ba_{0.2}Si_{10}$ in terms of atomic ratio when oxygen was excluded.

(Reaction)

A reaction was conducted with the catalyst in the same manner as in Example 12 except that the reaction temperature was changed to 360° C., after which analysis was made also in the same manner as in Example 12. One hour after the start of the reaction, the conversion of N-(2-hydroxyethyl)-2-pyrrolidone and the selectivity and per-pass yield of N-vinyl-2-pyrrolidone were 80.8 mole %, 97.8 mole % and 79.0 mole %, respectively.

EXAMPLE 29

(Catalyst Preparation)

150 g of water was added to 15.8 g of barium hydroxide octahydrate, 0.66 g of diammonium phosphate and 30 g of silicon oxide. The mixture was concentrated to dryness with stirring and heating on a water bath. The resulting material was dried in air at 120° C. for 20 hours and crushed into particles of 9–16 mesh, followed by calcining in air at 450° C. for 2 hours, to obtain a catalyst having a composition of $Ba_1Si_{10}P_{0.1}$ in terms of atomic ratio when oxygen was excluded.

(Reaction)

A reaction was conducted with the catalyst in the same manner as in Example 12, after which analysis was made also in the same manner as in Example 12. One hour after the start of the reaction, the conversion of N-(2-hydroxyethyl)-2-pyrrolidone and the selectivity and per-pass yield of N-vinyl-2-pyrrolidone were 67.2 mole %, 96.1 mole % and 64.6 mole %, respectively.

EXAMPLE 30

(Catalyst Preparation)

19.5 g of cesium nitrate and 4.9 g of boric acid were dissolved in 100 g of water. Thereto was added 30 g of silicon oxide. The mixture was concentrated to dryness with stirring and heating on a water bath. The resulting material was dried in air at 120° C. for 20 hours and crushed into particles of 9–16 mesh, followed by calcining in air at 500° C. for 2 hours, to obtain a catalyst having a composition of $Cs_1Si_5B_{0.8}$ in terms of atomic ratio when oxygen was excluded.

(Reaction)

With the catalyst, a reaction was continued for 100 hours in the same manner as in Example 12. One hour, 20 hours and 100 hours after the start of the reaction, the conversions of N-(2-hydroxyethyl)-2-pyrrolidone and the selectivities and per-pass yields of N-vinyl-2-pyrrolidone were as shown in Table 4.

TABLE 4

| Time (hour) | Conversion (mole %) | Selectivity (mole %) | Per-pass yield (mole %) |
| --- | --- | --- | --- |
| 1 | 84.5 | 96.0 | 81.1 |
| 20 | 83.8 | 96.6 | 81.0 |
| 100 | 82.0 | 98.0 | 80.4 |

EXAMPLE 31

(Catalyst Preparation)

19.5 g of cesium nitrate and 9.2 g of diammonium phosphate were dissolved in 100 g of water. Thereto were added 1.2 g of aluminum phosphate and 30 g of silicon oxide. The mixture was concentrated to dryness with stirring and heating on a water bath. The resulting material was dried in air at 120° C. for 20 hours and crushed into particles of 9–16 mesh, followed by calcining in air at 600° C. for 2 hours, to obtain a catalyst having a composition of $Cs_1Si_5Al_{0.1}P_{0.8}$ in terms of atomic ratio when oxygen was excluded.

(Reaction)

A reaction was conducted with the catalyst in the same manner as in Example 12, after which analysis was made also in the same manner as in Example 12. One hour after the start of the reaction, the conversion of N-(2-hydroxyethyl)-2-pyrrolidone and the selectivity and per-pass yield of N-vinyl-2-pyrrolidone were 53.6 mole %, 97.8 mole % and 52.4 mole %, respectively.

EXAMPLE 32–34

(Catalyst Preparation)

9.8 g of cesium nitrate and 5.3 g of diammonium phosphate were dissolved in 100 g of water. Thereto was added 30 g of silicon oxide. The mixture was concentrated to dryness with stirring and heating on a water bath. The resulting material was dried in air at 120° C. for 20 hours and crushed into particles of 9–16 mesh, followed by calcining in air at 500° C. for 2 hours, to obtain a catalyst having a composition of $Cs_1Si_{10}P_{0.8}$ in terms of atomic ratio when oxygen was excluded.

(Reaction)

Reactions were conducted with the catalyst in the same manner as in Example 12 except that the reaction conditions were changed as shown in Table 5, after which analyses were made in the same manner as in Example 12. One hour after the start of the reaction, the conversions of N-(2-hydroxyethyl)-2-pyrrolidone and the selectivities and per-pass yields of N-vinyl-2-pyrrolidone were shown in Table 5.

TABLE 5

| Ex. No. | Material partial pressure (mmHg) | Space velocity ($hr^{-1}$) | Reaction temp. (°C.) | Conversion (mole %) | Selectivity (mole %) | Per-pass yield (mole %) |
| --- | --- | --- | --- | --- | --- | --- |
| 32 | 76 | 200 | 400 | 78.9 | 96.8 | 76.4 |
| 33 | 76 | 100 | 400 | 89.9 | 93.3 | 83.9 |
| 34 | 38 | 200 | 390 | 92.1 | 98.4 | 90.6 |

EXAMPLE 35

(Catalyst Preparation)

8.15 g of cesium carbonate was dissolved 100 g of water. Thereto was added 30 g of silicon oxide. The mixture was concentrated to dryness with stirring and heating on a water bath. The resulting material was dried in air at 120° C. for 20 hours and crushed into particles of 9–16 mesh, followed by calcining in air at 500° C. for 2 hours, to obtain a catalyst having a composition of $Cs_1Si_{10}$ terms of atomic ratio when oxygen was excluded.

(Reaction)

5 ml of the catalyst was filled in a stainless steel-made reaction tube having an inside diameter of 10 mm. The reaction tube was dipped in a molten salt bath of 360° C. By providing a vacuum pump at the back end of the reaction tube, the outlet pressure of the reaction tube was controlled at 76 mmHg. Into this reaction tube was fed N-(2-hydroxyethyl)-2-pyrrolidone at a space velocity of 200 $h^{-1}$ to give rise to a reaction. After 100 hours of the reaction, the feeding of the raw material was stopped, and the pressure inside the reaction tube was returned to normal with nitrogen. Then, air was passed through the reaction tube at a rate of 100 cc/min for 24 hours to burn and remove the carbonaceous substance deposited on the catalyst, whereby the catalyst was regenerated. Thereafter, a reaction was conducted for 100 hours under the same conditions as mentioned above. The outlet gases of the reaction tube after 1 hour, 20 hours and 100 hours from the start of the raw material feeding and after 1 hour, 20 hours and 100 hours after the catalyst regeneration were analyzed by gas chromatography. The conversions of N-(2-hydroxyethyl)-2-pyrrolidone and the selectivities and per-pass yields of N-vinyl-2-pyrrolidone were as shown in Table 6.

TABLE 6

| Time (hour) | Conversion (mole %) | Selectivity (mole %) | Per-pass yield (mole %) |
| --- | --- | --- | --- |
| 1 | 94.3 | 94.9 | 89.5 |
| 20 | 93.5 | 95.6 | 89.4 |
| 100 | 93.0 | 96.4 | 89.7 |
| After regeneration | | | |
| 1 | 94.0 | 95.3 | 89.6 |
| 20 | 93.8 | 95.7 | 89.8 |
| 100 | 93.5 | 96.9 | 90.6 |

Examples 36–39 given below are each an example of production of a tertiary N-propenyl carboxylic acid amide by intramolecular dehydration of a tertiary N-(2-hydroxypropyl) carboxylic acid amide.

EXAMPLE 36

(Reaction)

A reaction was conducted with the catalyst of Example 1 in the same manner as in Example 1 except that the raw material for reaction was changed to N-(2-hydroxypropyl)-N'-methyl-acetamide, after which analysis was made also in the same manner as in Example 1. One hour after the start of the reaction, the conversion of N-(2-hydroxypropyl)-N'-methyl-acetamide and the selectivity and per-pass yield of N-propenyl-N'-methyl-acetamide [the total of N-(1-propenyl)-N'-methyl-acetamide and N-(2-propenyl)-N'-methyl-acetamide] were 67.9 mole %, 92.2 mole % and 62.6 mole %, respectively.

EXAMPLE 37

(Reaction)

A reaction was conducted in the same manner as in Example 36 except that the catalyst of Example 10 was used, after which analysis was made also in the same manner as in Example 36. One hour after the start of the reaction, the conversion of N-(2-hydroxypropyl)-N'-methyl-acetamide and the selectivity and per-pass yield of N-propenyl-N'-methyl-acetamide [the total of N-(1-propenyl)-N'-methyl-acetamide and N-(2-propenyl)-N'-methyl-acetamide] were 84.2 mole %, 94.5 mole % and 79.6 mole %, respectively.

EXAMPLE 38

(Reaction)

A reaction was conducted in the same manner as in Example 36 except that the catalyst of Example 17 was used and the raw material for reaction was changed to N-(2-hydroxypropyl)-N'-methyl-propylamide, after which analysis was made also in the same manner as in Example 36. One hour after the start of the reaction, the conversion of N-(2-hydroxypropyl)-N'-methyl -propylamide and the selectivity and per-pass yield of N-propenyl-N'-methyl-propylamide [the total of N-(1-propenyl)-N'-methyl-propylamide and N-(2-propenyl)-N'-methyl-propylamide] were 93.1 mole %, 91.6 mole % and 85.3 mole %, respectively.

EXAMPLE 39

(Reaction)

A reaction was conducted in the same manner as in Example 38 except that the catalyst of Example 31 was used, after which analysis was made also in the same manner as in Example 38. One hour after the start of the reaction, the conversion of N-(2-hydroxypropyl)-N'-methyl-propylamide and the selectivity and per-pass yield of N-propenyl-N'-methyl-propylamide [the total of N-(1-propenyl)-N'-methyl-propylamide and N-(2-propenyl)-N'-methyl-propylamide] were 60.4 mole %, 95.6 mole % and 57.7 mole %, respectively.

As illustrated with the above Examples, the catalyst of the present invention enables continuous and efficient production of a tertiary N-alkenyl carboxylic acid amide from a tertiary N-(2-hydroxyalkyl) carboxylic acid amide without using any auxiliary raw material. Therefore, the present process for production of a tertiary N-alkenyl carboxylic acid amide is simple because no auxiliary raw material is used, and is safe because no by-product (no waste product) derived from said auxiliary raw material is generated.

What is claimed is:

1. A process for producing a tertiary N-alkenyl carboxylic acid amide by gas-phase intramolecular dehydration of a tertiary N-(2-hydroxyalkyl) carboxylic acid amide in the presence of a catalyst which is an oxide comprising silicon and at least one element selected from the group consisting of alkali metals and alkaline earth metals.

2. The process according to claim 1, wherein the catalyst is an oxide represented by the following general formula (1)

  (1)

wherein

M is at least one element selected from the group consisting of alkali metals and alkaline earth metals;

Si is silicon;

X is at least one element selected from the group consisting of boron, aluminum and phosphorus;

O is oxygen;

a, b, c and d are each the number of atoms of the corresponding element with provisos that when a=1, b=1–500 and c=0–1 and d is a number determined by the values of a, b and c and the condition in which the individual constituent elements are bonded to each other.

3. The process according to claim 1 or 2, wherein tertiary N-(2-hydroxyalkyl) carboxylic acid amide is an N-(2-hydroxyethyl)-N'-alkyl-amide compound represented by the following general formula (2)

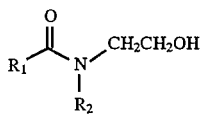  (2)

wherein $R_1$ and $R_2$ are independently a hydrocarbon group of 1–6 carbon atoms, and the tertiary N-alkenyl carboxylic acid amide is an N-vinyl-N'-alkyl-amide compound represented by the following general formula (3)

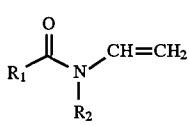  (3)

wherein $R_1$ and $R_2$ have the same definitions as for the general formula (2).

4. The process according to claim 1 or 2, wherein the tertiary N-(2-hydroxyalkyl) carboxylic acid amide is N-(2-hydroxyethyl)-2-pyrrolidone and the tertiary N-alkenyl carboxylic acid amide is N-vinyl-2-pyrrolidone.

5. The process according to claim 1 or 2, wherein the tertiary N-(2-hydroxyalkyl) carboxylic acid amide is an N-(2-hydroxyalkyl)-N'-alkyl-amide compound represented by the following general formula (4)

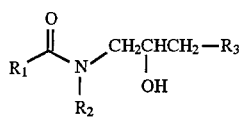  (4)

wherein $R_1$, $R_2$ and $R_3$ are independent groups with $R_1$ and $R_2$ each being a hydrocarbon group of 1–6 carbon atoms and $R_3$ being a hydrogen atom or a hydrocarbon group of 1–6 carbon atoms, and the tertiary N-alkenyl carboxylic acid amide is an N-alkenyl-N'-alkyl-amide compound represented by the following general formulas (5) and (6)

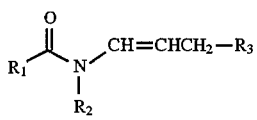  (5)

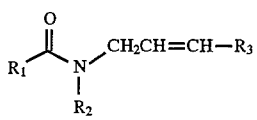  (6)

wherein $R_1$, $R_2$ and $R_3$ each have the same definitions as for the general formula (4).

6. A process for producing a tertiary N-alkenyl carboxylic acid amide by gas-phase intramolecular dehydration of a tertiary N-(2-hydroxyalkyl) carboxylic acid amide in the presence of an oxide catalyst consisting of oxygen, silicon and at least one element selected from the group consisting of alkali metals and alkaline earth metals.

* * * * *